United States Patent
Halter et al.

(10) Patent No.: US 11,199,546 B2
(45) Date of Patent: Dec. 14, 2021

(54) STRATIFICATION OF PATIENTS FOR ASSESSING THE SUITABILITY OF A THERAPY

(71) Applicant: KONINKLIJKE PHILIPS N.V., Eindhoven (NL)

(72) Inventors: David Halter, Eindhoven (NL); Reinhold Wimberger-Friedl, Eindhoven (NL); Anja Van De Stolpe, Eindhoven (NL); Freek Van Hemert, Eindhoven (NL); Geeske Christina Dam-De Veen, Eindhoven (NL)

(73) Assignee: KONINKLIKE PHILIPS N.V., Eindhoven (NL)

( * ) Notice: Subject to any disclaimer, the term of this patent is extended or adjusted under 35 U.S.C. 154(b) by 1123 days.

(21) Appl. No.: 15/111,328

(22) PCT Filed: Jan. 21, 2015

(86) PCT No.: PCT/EP2015/051051
§ 371 (c)(1),
(2) Date: Jul. 13, 2016

(87) PCT Pub. No.: WO2015/110440
PCT Pub. Date: Jul. 30, 2015

(65) Prior Publication Data
US 2016/0334405 A1 Nov. 17, 2016

(30) Foreign Application Priority Data
Jan. 22, 2014 (EP) .................................... 14152183

(51) Int. Cl.
*G01N 31/00* (2006.01)
*G01N 33/53* (2006.01)
*G01N 33/574* (2006.01)
*G01N 33/74* (2006.01)

(52) U.S. Cl.
CPC ..... *G01N 33/57415* (2013.01); *G01N 33/574* (2013.01); *G01N 33/57434* (2013.01); *G01N 33/743* (2013.01); *G01N 2800/52* (2013.01)

(58) Field of Classification Search
None
See application file for complete search history.

(56) References Cited

U.S. PATENT DOCUMENTS

| 2010/0196906 A1 | 8/2010 | Buechler |
| 2012/0121360 A1 | 5/2012 | Ehrler |
| 2013/0130279 A1 | 5/2013 | Fantl |

FOREIGN PATENT DOCUMENTS

| WO | 200111361 A2 | 2/2001 |
| WO | 2008019375 A2 | 2/2008 |
| WO | 2009089521 A1 | 7/2009 |
| WO | 2014016401 A1 | 1/2014 |

OTHER PUBLICATIONS

Trevino and Weigel (Trends in Endocrinology and Metabolism, Oct. 2013, vol. 24, No. 10, pp. 515-524).*
Tascilar et al. (Annals of Oncology 10,Suppl. 4:S107-S110, 1999).*
Tockman et al. (Cancer Research 52:2711s-2718s, 1992).*
Poulard, Coralie et al "Activation of Rapid Oestrogen Signalling in Aggressive Human Breast Cancers", EMBO Molecular Medicine, vol. 4, 2012, pp. 1200-1213.
Diaz Flaque, Maria C. et al "Progesterone receptor assembly of a transcriptional complex along with activator protein 1, signal transducer and activator of transcription 3 and ErbB-2 governs breast cancer growth and predicts response to endocrine therapy", Breast Cancer Research, vol. 15, 2013, pp. 1-24.
Bostner, Josefine "The Akt/mTOR Pathway and Estrogen Receptor Phosphorylations—a Crosstalk with Potential to Predict Tamoxifen Resistance in Breast Cancer", 2013.
Musgrove, Elizabeth A., et al, Biological Determinants of Endocrine Resistance in Breast Cancer, Nature Reviews Cancer, vol. 9, pp. 631-643. 2009.
The Proximity Ligation Assays: A recent Addition to the proteomics toolbox. Expert Rev. Proteomics, vol. 7, No. 3, 2010, pp. 401-409.
Flach, Koen D. et al "PKA phosphorylation redirects ERa to promoters of a unique gene set to induce tamoxifen resistance", Oncogene, vol. 32, 2013, pp. 3543-3551.
Miller, Todd W. et al "Hyperactivation of phosphatidylinositol-3 kinase promotes escape from hormone dependence in estrogen receptor-positive human breast cancer", The Journal of Clinical Investigation, vol. 120, No. 7, 2010, pp. 2406-2413.
Geyer, Felipe C. et al "Genetic Characterization of Breast Cancer and Implications for Clinical Management", Journal Cell. Mol. Medicine, vol. 13, No. 10, 2009, pp. 4090-4103.
Mukherjee, Abhik et al "Integrating Breast Cancer Genetics into Clinical Practice", Women's Health, vol. 8, No. 1, pp. 99-112, 2012.

* cited by examiner

Primary Examiner — Lisa V Cook (57) ABSTRACT

A method for stratification of a patient for assessing suitability of a therapy for the patient suffering from an ER (estrogen receptor) and/or PR (progesterone receptor) positive and HER2 (human epidermal growth factor receptor 2) negative cancer, the therapy being directed towards a signaling pathway, includes: (i) determining an activation status of an ER and/or PR signaling pathway by applying a Proximity Ligation Assay to detect in a tissue sample of the patient a presence of at least one member of the ER family, the at least one member being part of a transcription factor complex, and at least one protein selected from a group consisting of TAFs (TATA-binding protein associated factor), TBP (TATA-box binding protein), POLII (RNA polymerase II), TFII (transcription factor H), p300, CREB (cyclic-AMP response element-binding protein), and CBP (CREB binding protein), wherein the at least one protein is part of the same transcription factor complex.

7 Claims, 4 Drawing Sheets

STRATIFICATION OF PATIENTS FOR ASSESSING THE SUITABILITY OF A THERAPY

CROSS-REFERENCE TO PRIOR APPLICATIONS

This application is the U.S. National Phase application under 35 U.S.C. § 371 of International Application No. PCT/EP2015/051051, filed on Jan. 21, 2015, which claims the benefit of European Patent Application No. 14152183.1, filed on Jan. 22, 2014. These applications are hereby incorporated by reference herein.

FIELD OF THE INVENTION

The present invention primarily relates to an improved method for stratification of a patient, preferably a cancer patient, for assessing the suitability of a therapy, such as a targeted therapy, for the patient, the therapy preferably being directed towards the estrogen receptor (ER) and/or progesterone receptor (PR) signaling pathway (other suitable pathways are described herein below). The present invention further relates to a method for the prognosis of the outcome of a disease, preferably cancer, of a patient, preferably a cancer patient, and a method for the prediction and/or detection of therapy resistance of a patient, preferably a cancer patient, towards a therapy. Furthermore, the invention relates to a novel kit, and corresponding uses thereof.

BACKGROUND OF THE INVENTION

The article, "Biological determinants of endocrine resistance in breast cancer" by Musgrove et al., *Nature Reviews Cancer*, Volume 9, pages 631 to 643 (2009) discloses cell signaling pathways associated with the failure of endocrine/hormonal therapies targeting estrogen action. The methods disclosed in this paper to show if certain pathways are active should be improved for purposes of improved diagnosis and therapy response prediction in the medical field.

The article, "Progesterone receptor assembly of a transcriptional complex along with activator protein 1, signal transducer and activator of transcription 3 and ErbB-2 governs breast cancer growth and predicts response to endocrine therapy" by Díaz Flaqué et al., *Breast Cancer Research*, Volume 15, Number 6, page R118 (2013) investigates coordinated PR rapid and non-classical transcriptional effects governing breast cancer growth and endocrine therapy resistance.

The article, "Activation of rapid oestrogen signalling in aggressive human breast cancers", by Poulard et al., *EMBO Molecular Medicine*, Volume 4, Number 11, pages 1200 to 1213 (2012) reports on the detection of endogenous ERα/PI3K and ERα/Src interactions in human breast tumour cells.

The dissertation, "The Akt/mTOR Pathway and Estrogen Receptor Phosphorylations a crosstalk with potential to predict tamoxifen resistance in breast cancer", *Linköping University Medical Dissertations*, No. 1379 (2013) concerns the investigation of biomarkers, as a complement to the existing markers, for determining optimal treatment for patients with primary invasive breast cancer.

SUMMARY OF THE INVENTION

Current staining assays are based on staining the expression of one protein (not an (active) transcription factor or, respectively, transcription factor complex) in the cell or in a specific location in the cancer cell, like for example ER staining in the cell nucleus, which is known to be associated with activation of the ER pathway and with therapy response when a drug is used which targets the ER pathway. However such single protein staining does not provide proof of an active pathway. For example in the case of ER, the single protein can also be present in the nucleus when not in an active ER transcription factor complex.

Routine pathology staining in breast cancer entails ER, PR and HER2 staining ER and PR are usually considered to be positive if more than 1% (US) or 10% (EU) of cancer cells express nuclear ER or PR, respectively. This is used as indication that these pathways are active in the respective patients. The minimal percentage of positive cancer cells required for a positive test result varies between different centers. These patients are considered to be candidates for hormonal (anti ER pathway) therapy. ER positive patients are treated with hormonal therapy (in a neoadjuvant, adjuvant, or metastatic setting); however 25-50% of the patients do not respond or become resistant to treatment. Thus, assays for improved therapy response prediction are required.

Such conventional ER staining is also used for prognostic purposes. However, within the ER positive group many patients appear to have a worse prognosis than originally predicted. This requires improved prognostic assays.

Within the ER positive group of patients which do not respond to anti ER pathway therapy, either primary or secondary, multiple biochemical resistance mechanisms have been described, which are associated with another tumor driving signaling pathway instead of the ER pathway, e.g. the HER2 pathway, Wnt pathway, HH (hedgehog) pathway etc. (details regarding resistance will be described herein further below). Assays are needed which indicate the resistance pathway(s) in ER positive patients resistant to hormonal therapy.

In view of the above, it is a primary object of the present invention to provide an improved method for stratification of a patient, preferably a cancer patient, in particular a breast cancer or prostate cancer patient, especially an ER and/or PR positive and HER2 negative breast cancer patient, for assessing the suitability of a therapy, such as a hormonal therapy, for the patient, the therapy being preferably directed towards the ER and/or PR signaling pathway. Further signaling pathways that may be addressed in connection with the present invention include, but are not limited to, the androgen receptor (AR) signaling pathway, the retinoic acid receptor (RAR) signaling pathway, the VitD pathways, and the peroxisome proliferator-activated receptor (PPAR) signaling pathway. Further objects of the present invention relate to the provision of improved methods for the prognosis of the outcome of a disease, preferably cancer, of a patient, preferably a cancer patient, and for the prediction and/or detection of therapy resistance of a patient, preferably a cancer patient, towards a specific therapy. Additional objects underlying the present invention become apparent when studying the following specification and, in particular, the attached patent claims.

The primary object of the present invention is achieved by a method for stratification of a patient, preferably a cancer patient, for assessing the suitability of a therapy, preferably a hormonal therapy, for the patient, the therapy preferably being directed towards the estrogen receptor (ER) and/or progesterone receptor (PR) signaling pathway, comprising the step of (i) determining the activation status of an ER and/or PR signaling pathway by applying a Proximity Ligation Assay to detect in a tissue sample, preferably in a tumor tissue sample, more preferably in a biopsy sample of the patient the presence of at least one member of the ER family, said at least one member being part of a transcription factor complex, and at least one protein selected from the group consisting of TAFs, TBP, POLII, TFII, p300, CREP1, and CBP, wherein the at least one protein is part of the same transcription factor complex, wherein the stratification is based on the activation status determined in step (i) and the suitability of the therapy is assessed based on the stratification.

Preferred embodiments of such a method are described in the claims and herein below.

With respect to the ERs (cf. above), there are two different forms of ERs, usually referred to as α and β, each encoded by a separate gene (ESR1 and ESR2, respectively). Hormone-activated estrogen receptors form dimers, and, since the two forms are coexpressed in many cell types, the receptors may form ERα (αα) or ERβ (ββ) homodimers or ERαβ (αβ) heterodimers. Thus, the at least one family member of the ER family is preferably selected from the group consisting of ERα, ERβ, to form either ERαα (homodimer), ERββ (homodimer), and ERαβ (heterodimer), or a heterodimer with another transcription factor, like for example a member of the AP1 (Fos, Jun) or NFkappaB family, or CREB, wherein for the purposes of the present invention at least one member is preferably an ER protein.

As mentioned above, said at least one member of the ER family to be preferably detected in connection with a method of the present invention is part of a transcription factor complex. The term "transcription factor complex" means a complex comprising or consisting of at least two transcription factors or, respectively, proteins. For example, such a transcription factor complex may consist of one or more homo- and/or heterodimers, preferably an ER monomer or dimer, and/or one or more, preferably two or more, proteins selected form the above defined group (e.g. p300).

The activity status of the PR pathway can be determined similarly to the way described above. There are two progesterone receptors, PR-A and PR-B, which become activated by binding of the ligand progesterone, which transforms the receptors into active transcription factors which analogous to the ER bind coactivators like CREB/p300 and bind to specific response elements in the promoter region of target genes, from which mRNA is made.

The method according to the present invention (as described herein) is particularly suitable for stratification of a cancer patient, in particular for stratification of a breast cancer or prostate cancer patient, especially of an ER and/or PR positive and HER2 negative breast cancer patient. In particular, the method according to the present invention can be advantageously used for assessing the suitability of a hormonal therapy for the patient.

Cancer is a leading cause of death worldwide, accounting for 7.6 million deaths (around 13% of all deaths) in 2008. Of those, 458000 deaths were supposedly caused by breast cancer. Breast cancer is the most common cancer in women worldwide (approx. 16% of all cancers in women), but it can also affect men, however much less frequently (only 1 in ~100 breast cancers is diagnosed in a male). Several different forms of breast cancer exist and therefore also need different treatments. The traditional way of treating breast cancers has been surgical removal of the (primary) tumor, often combined with adjuvant chemotherapy and/or radiation therapy. A better understanding of the disease mechanisms has led to a paradigm shift towards so-called targeted therapies (also described as personalized therapies, personalized medicine or precision medicine) in which cells are not killed unselectively (causing severe side effects), but in which cells containing a defect responsible for disease are attacked very specifically.

The most prominent example for such a targeted treatment is Herceptin (a.k.a. Trastuzumab) by Genentech/Roche. Herceptin binds the HER2 receptor (a.k.a. HER2/neu or erbb2). HER2 overexpression leads to hyperactivation of cellular signaling (most prominent: PI3K-pathway and MAPK-pathway) that finally lead to aberrant cell growth.

Another example has been the treatment of breast cancer in which a defined (>1-10%; cf. above) percentage of cancer cells express ER and/or PR. These receptors can activate respectively the ER and PR signaling pathway. Those cases are treated with hormonal (or endocrine) therapies. Those therapies are blocking the production of estrogen or compete with estrogen for the limited ER binding sites (e.g. Tamoxifen is such an estrogen analogue).

For the initial diagnosis (i.e. defining whether or not cancer is present) usually a hematoxylin and eosin (H&E) staining is performed on a biopsy sample or a thin slice of the suspicious tissue. The tissue comprises either fresh-frozen tissue or, more commonly, formalin-fixed-paraffin-embedded (FFPE) tissue.

If a cancer has been diagnosed, further tests need to be performed in order to decide which kind of targeted therapy (if any at all) could benefit a patient. In current guidelines (e.g. National comprehensive clinical network (NCCN) guidelines for treating breast cancer) histopathological testing for the presence/overexpression of the above mentioned receptor molecules (HER2, ER, PR) is described as follow-up. These tests are usually done in the form of an immunohistochemistry (IHC) assay performed on tissue slides from the same tissue sample/block as the H&E staining for diagnosis, but on a different thin slice of that sample. As an alternative for e.g. HER2-IHC (or if the IHC result is ambiguous), in situ hybridization (ISH) is frequently performed to measure amplification of the HER2-gene.

According to these tests, a patient is then stratified as belonging into one of the four following breast cancer classes:

(1) Positive for either ER or PR (or both) AND negative for HER2
 → hormone receptor positive breast cancer
(2) Negative for both ER AND PR, BUT positive for HER2
 → HER2 positive breast cancer
(3) Positive for either ER or PR (or both) AND positive for HER2
 → hormone receptor and HER2 positive breast cancer
(4) Negative for all receptors
 → so called triple negative breast cancer (Side remark: if either ER or PR are positive, then it can be called hormone receptor positive (without mentioning whether ER or PR is meant), as it has (currently) the same implications for treatment).

Although being not limited to breast cancer patients, the present invention focuses—according to one aspect of the invention on the stratification of breast cancer patients, especially on breast cancer patients belonging to class (1) of the above described breast cancer classes (i.e. ER/PR+ and HER2−). Class (1) is the most prevalent type in breast cancer.

Depending on for which marker a patient is tested positive, i.e. depending on which of the aforementioned breast cancer classes a patient belongs to, a different treatment is the therapy of choice. Independent of those markers it needs to be decided whether chemotherapy and/or radiation therapy has to be applied. Based on the mentioned markers or, respectively, classes, it can be decided whether one of the targeted therapies can/should be applied:

(1): If a patient is tested positive for expression of ER or PR, endocrine treatment is the therapy of choice. The kind of treatment then depends again on the hormonal status of a patient, in the first line of whether a patient is pre- or post-menopausal.

If a drug-based approach is chosen the following possibilities exist:
(i) using selective estrogen receptor modulators (SERM), which work by blocking estrogen binding to estrogen receptors in breast tissue (antagonist action while having agonist action in other tissues); best known example: Tamoxifen;
(ii) using aromatase inhibitors (AI), which prevent the body from making estrogen via the enzyme aromatase; examples are: Arimidex (anastrazole), Aromasin (exemestane), Femara (letrozole) and Fadrozole;
(iii) using estrogen receptor antagonists, which work by down regulating the estrogen receptor; example: Fulvestrant.

(2): Patients positive for HER2 can get a HER2-specific treatment, which comprises either antibodies specific for HER2 (or HER2 family) receptors, such as Trastuzumab and Pertuzumab or a tyrosine kinase inhibitor (TKI), such as Lapatinib, or combinations thereof (3): If a patient is positive for both HER2 and either one of the hormone receptors, combination of the treatments mentioned in (1) and (2) is chosen, as both conditions are targeted.

(4): All three receptors are tested negative; this means that none of the targeted therapies is applied and alternative approaches have to be chosen, like chemotherapy.

Although IHC has a proven clinical value, it is limited with respect to the fact that the mere presence of a protein gives no indication about its signaling activity. Usually, in order to be able to tell whether a protein is actively signaling or not, one needs a method to detect its phosphorylation status or whether it is forming complexes with other proteins.

Relevant interactions are therefore, inter alia, posed by aggregates of multiple proteins whose interaction may indicate the activation of a certain pathway (transcription factor complexes). Their proximity is possibly relevant information for the identification of a tumor driving pathway and thus the treatment of said tumor. In the canonical ER pathway for example, ER enters the nucleus as a dimer, which can be detected using PLA. After entering the nucleus, a transcription factor complex is formed involving many factors (cf. FIG. 1), any two of which may serve as the basis (targets) for a PLA assay. The mere presence of ER or for example the general cofactor p300 in the nucleus may be meaningless while their close proximity is indicative of the formation of a fully functional transcription factor complex and thus active transcription of a set of genes.

In addition to the above, the Proximity Ligation Assay allows for several further advantages, such as making image analysis and quantification easier and more reliable compared to IHC/IF. In particular, the Proximity Ligation Assay produces discrete signals (dots), single molecular interactions can be measured (due to signal amplification in situ), a high sensititivity is obtained, and there are less problems with background signals/auto-fluorescence (the signal can be separated easier from noise (dots vs. "smear")). Furthermore, improved and simplified image analysis facilitates automated image analysis and more accurate quantification.

The Proximity Ligation Assay (compare Weibrecht et al, *Expert Rev. Proteomics*, 7(3), pages 401-409 (2010); "Proximity ligation assays: a recent addition to the proteomics toolbox" (included herein via reference), an animation of the method can be found online such as YouTube (trademark) is a method that is capable of reporting on the co-location of two protein epitopes. The method uses two antibodies labeled with a DNA oligo. The oligos are both needed to form a closed circle out of two secondary DNA oligos which are added to the sample after the antibodies have found their epitopes. Once a closed loop is formed, Rolling Circle amplification (RCA) is used to make hundreds of copies of the circular probe. Later, a complementary probe, labeled with a fluorophore, is annealed to the RCA product yielding a very bright spot in the place where the two proteins are co-located.

For example, the Duolink Proximity Ligation Assay from Olink S. A., Sweden, may be used in connection with the present invention. However, other possibilities are not excluded As indicated above, a key problem in cancer treatment is that a large percentage of breast cancer patients belonging into class (1) (as described above) do not react to the therapies described above (ER antagonist, SERMs or AIs) or become resistant after a while, such resistance being often mediated by other pathways becoming activated. For example, one way for cells to escape hormone dependence in ER+ breast cancer is the hyperactivation of the PI3K-pathway. In other words, in those cells not the ER pathway is driving the cancer anymore, but the PI3K pathway has taken over and should be targeted by therapy instead. Switching from an ER alpha to ER alpha/ER beta heterodimer or ER beta homodimer may also be a way to induce resistance to a drug. Further mechanisms of resistance exist and additional examples will be described further below, in particular in connection with preferred embodiments of methods according to the present invention (cf., in particular, steps (ii) to (vi) as described further below).

Furthermore, the (mere) detection of an overexpression of the ER receptor is no proof that the ER signaling is responsible for disease progression. In this respect, a clear shortcoming of today's approach as known in the prior art is that current ER diagnostic tests cannot determine whether the ER pathway is actually active in the cancer cells where ER is detected. This decreases the value to correctly classify patients with the desired specificity for the appropriate treatment.

The above problems or, respectively, shortcomings are addressed by the method according to the present invention (as described herein), which, for example, allows an accurate determination of the activity of the (canonical) ER-pathway and, preferably, also of relevant "escape" or, respectively, "resistance" pathways (as in particular described further below in connection with preferred embodiments of a method according to the present invention).

The inventors have found that by using the herein described method of the present invention it is possible to measure the actual activation status of typical pathways, like the canonical ER pathway, on protein levels in cells in a tissue sample standardly used for histopathology diagnostics (in contrast to the standardly used method in which the nuclear presence of the ER protein alone is taken as indicative for ER pathway activation).

Further, it is possible with the method of the present invention (as described herein) to get spatial and single cell information from the tissue sample whereas the approaches described by Musgrove et al. average the signal over a whole sample. For example, gaining spatial information at a single cell level is necessary to determine in which cells in the tissue the ER pathway is activated, e.g. to calculate the percentage of the cells with activated ER pathway. By e.g. combining the method of the invention with other tissue biomarker stainings it will be possible to identify which biomarkers are active together in one cell, which can be important for therapy choice. In comparison, this is not possible when pathway activity is inferred from RNA/DNA isolated from a tissue slide. Such other biomarkers may for example be a DNA mutation or a signaling protein or transcription factor of another pathway, which may confer resistance to the hormonal therapy if present in the same cell.

As indicated above, the (cancer) patient stratified as described herein is preferably a breast cancer or a prostate cancer patient and, consequently, the tissue sample to be used in connection with a method of the invention (as described herein) is preferably from a breast cancer or a prostate cancer patient. Further preferred is a method of the present invention, wherein the cancer patient is an ER and/or PR positive and HER2 negative breast cancer patient and, consequently, the tissue sample is from an ER and/or PR positive and HER2 negative breast cancer patient.

Advantageously, the method of the present invention is particularly suitable to not only determine the activity status of an ER and/or PR signaling pathway, but also to assess potential mechanisms of resistance to hormonal therapy. In this respect, it is preferred that the method of the invention additionally comprises the step of determining the activity of one or more "escape" or "resistance" pathways, or, respectively, mechanisms. Preferred embodiments and steps of such methods are described below.

Preferably, the method of the present invention additionally comprises at least one, i.e. one, more or all of the following steps:
(ii) determining the activation status of a signaling pathway, which is different from the signaling pathway assessed in step (i), by applying an in-situ staining assay, preferably a Proximity Ligation Assay, to detect in the same or in a different tissue sample of the (cancer) patient the presence of at least one member of the ER family and at least one protein selected from the group consisting of c-Fos, c-Jun (AP1), SP1, CREB, GATA-transcription factor, NFkappaB family, c/EBP proteins, FOXO, SMAD transcription factor proteins, preferably wherein said at least one member of the ER family and said at least one protein are part of the same transcription factor complex,
wherein the stratification is further based on the activation status determined in step (ii),
(iii) determining the phosphorylation status of at least one member of the ER family at serine 305 in the tissue sample of the (cancer) patient,
wherein the stratification is further based on the phosphorylation status determined in step (iii),
(iv) determining the activation status of one or more signaling pathways, which is/are different from the signaling pathway assessed in step (i) and is/are selected from the group consisting of PI3K pathway, Wnt pathway, HH pathway, NFkappaB, Notch pathway, TGFbeta, FGF, VEGF, EMT, pathways, other nuclear receptor pathways, like the AR, RAR, PPAR, glucocorticoid, VitD pathways, by applying an in-situ staining assay, preferably a Proximity Ligation Assay, wherein the same or a different tissue sample of the (cancer) patient is used,
wherein the stratification is further based on the activation status determined in step (iv),
(v) determining the activation status of the PI3K pathway by applying an in-situ staining assay, preferably a Proximity Ligation Assay, to detect in the same or in a different tissue sample of the (cancer) patient an active PKB/Akt protein by measuring the phosphorylation status of PBK/Akt, preferably at threonine 308 and/or serine 473,
wherein the stratification is further based on the activation status determined in step (v), and
(vi) applying an in-situ staining assay, preferably a Proximity Ligation Assay, to detect in the same or in a different tissue sample of the (cancer) patient the presence of at least one member of the ER family and at least one component, preferably a transcription factor, wherein the at least one component or, respectively, transcription factor is expected to be present at any ERE (Estrogen Response Element) half-site or any non-ERE site and/or wherein the at least one component or, respectively, transcription factor is selected from the group consisting of AP1 (c-Fos, c-Jun), cAMP response element-binding protein/CREB, GATA transcription factor, and NFkappaB, SP1, C/EBP, FOXO, SMAD transcription factor proteins,
wherein the stratification is further based on the detection in step (vi).

Depending on the intended purpose of the method according to the invention as described herein and/or, respectively, depending on the type of (cancer) patient, the type of therapy, the suitability of which has to be assessed, and/or the signaling pathway, the activation of which has to be determined, step (iv) (as described above) may also be performed instead of or, respectively, as step "(i)" (as described introductorily).

Step (ii) is based on the knowledge that the Estrogen-ER complex can not only bind directly to estrogen response elements (ERE's) in promoter regions of genes, but may act as a co-factor at non-ERE sites interacting with other DNA-binding elements such as c-Jun or c-Fos. (In this regard, cf. also step (vi) which generally refers to transcription factors expected to be present at any non-ERE site or any ERE half-site, e.g. AP1.)

Another possible mechanism of resistance to hormonal therapy (e.g. to Tamoxifen treatment), which is addressed by the above described step (iii), is the phosphorylation of the serine on position 305 in ER (the region between the ligand and DNA binding domain.). Determining the phosphorylation status of ER is preferably performed by using a PLA. In this regard, ER specific antibodies are available that may be used, e.g. antiERαS305-P (available from Millipore/Upstate).

According to a particularly preferred embodiment of the invention the method of the invention additionally comprises the step of determining the activation status of the PI3K pathway, the Wnt pathway, and/or the HH pathway (cf. above, step (iv)). Those pathways may also have influence on potential resistance or, respectively, may be indicative of such resistance. For those pathways also specific transcription factors can be determined and preferably detected via the PLA method. The PI3K-pathway is of particular interest. This pathway is preferably tested in addition to the ER transcription factor complex involving pathway. Accordingly, a method of the invention preferably additionally comprises step (v) as described above. The test outcome is then defined as pAkt positive or pAkt negative. Alternatively, e.g. also transcription factors of the PI3K-pathway from the FOXO class can be determined.

Particularly preferred is a method according to the present invention, wherein the method focuses on determining the activation status of an ER pathway by detecting an ER transcription factor complex and additionally determining the activation status of the PI3K pathway. Thus, a method of the invention preferably comprises the following steps:
(i) determining the activation status of an ER and/or PR signaling pathway by applying a Proximity Ligation Assay to detect in a tissue sample of the cancer patient the presence of at least one member of the ER family, preferably an ER dimer, said at least one member being part of a transcription factor complex, and at least one protein selected from the group consisting of TAFs, TBP, POLII, TFII, p300, CREP1, and CBP, preferably p300, wherein the at least one protein is part of the same transcription factor complex, and
(v) determining the activation status of the PI3K pathway by applying an in-situ staining assay, preferably a Proximity Ligation Assay, to detect in the same tissue sample of the cancer patient an active PKB/Akt protein by measuring the phosphorylation status of PBK/Akt, wherein the stratification is based on the activation status determined in step (i) and the activation status determined in step (v), preferably wherein (as mentioned above) the cancer patient preferably is a breast cancer patient, especially an ER and/or PR positive and HER2 negative breast cancer patient and, respectively, the tissue sample preferably is from a breast cancer patient, especially from an ER and/or PR positive and HER2 negative breast cancer patient.

The term "tissue sample" as used herein preferably refers to a biopsy sample of a patient (such as for example a biopsy sample obtained by/from cytology, liquid biopsy, blood cells, resected tumor tissue, or fine needle biopsy), more preferably a tumor tissue sample of a patient, in particular a cancer patient. In case a tumor tissue sample is used in connection with a method of the present invention, such a tumor tissue sample is preferably selected from the group consisting of fresh frozen (FF) tumor tissue sample and formalin-fixed paraffin-embedded (FFPE) tumor tissue sample and/or from the group consisting of a thin section of a resected tumor, a thin section of a biopsy sample, captured circulating tumor cells (CTCs) and fine needle aspirates. On those tissue samples the method according to the invention can be performed easily and effectively.

A further aspect of the present invention relates to a method for the prognosis of the outcome of a disease, preferably cancer, of a patient, preferably a cancer patient, wherein the method comprises determining the activation status of an ER and/or PR signaling pathway by applying a Proximity Ligation Assay, wherein the method comprises at least step (i) as defined above, wherein the prognosis is based on the determined activation status.

Another aspect of the present invention relates to a method for the prediction and/or detection of therapy resistance of a patient, preferably a cancer patient, towards a therapy, such as a hormonal therapy, the therapy preferably being directed towards the ER and/or PR signaling pathway, wherein the method comprises determining the activation status of an ER and/or PR signaling pathway by applying a Proximity Ligation Assay, wherein the method comprises at least step (i) as defined above, wherein the prediction and/or detection is based on the determined activation status.

Such methods may also comprise one, more or all of the above described additional steps (ii) to (vi). Particularly preferably, such methods additionally comprise one or more of the following steps:
(ii) determining the activation status of a signaling pathway, which is different from the signaling pathway assessed in step (i), by applying an in-situ staining assay, preferably a Proximity Ligation Assay, to detect in the same or in a different tissue sample of the (cancer) patient the presence of at least one member of the ER family and at least one protein selected from the group consisting of c-Fos, c-Jun (AP1), SP1, CREB, GATA-transcription factor, NFkappaB family, c/EBP proteins, FOXO, SMAD transcription factor proteins, preferably wherein said at least one member of the ER family and said at least one protein are part of the same transcription factor complex, wherein the prognosis resp. the prediction and/or detection is further based on the activation status determined in step (ii),
(iii) determining the phosphorylation status of at least one member of the ER family at serine 305 in the tissue sample of the (cancer) patient, wherein the prognosis resp. the prediction and/or detection is further based on the phosphorylation status determined in step (iii),
(iv) determining the activation status of one or more signaling pathways, which is/are different from the signaling pathway assessed in step (i) and is/are selected from the group consisting of PI3K pathway, Wnt pathway, HH pathway, NFkappaB, Notch pathway, TGFbeta, FGF, VEGF, EMT, pathways, other nuclear receptor pathways, like the AR, RAR, PPAR, glucocorticoid, VitD pathways, by applying an in-situ staining assay, preferably a Proximity Ligation Assay, wherein the same or a different tissue sample of the (cancer) patient is used, wherein the prognosis resp. the prediction and/or detection is further based on the activation status determined in step (iv),
(v) determining the activation status of the PI3K pathway by applying an in-situ staining assay, preferably a Proximity Ligation Assay, to detect in the same or in a different tissue sample of the (cancer) patient an active PKB/Akt protein by measuring the phosphorylation status of PBK/Akt, preferably at threonine 308 and/or serine 473, and wherein the prognosis resp. the prediction and/or detection is further based on the activation status determined in step (v),
(vi) applying an in-situ staining assay, preferably a Proximity Ligation Assay, to detect in the same or in a different tissue sample of the (cancer) patient the presence of at least one member of the ER family and at least one component, preferably a transcription factor, wherein the at least one component or, respectively, transcription factor is expected to be present at any ERE (Estrogen Response Element) half-site or any non-ERE site and/or wherein the at least one component or, respectively, transcription factor is selected from the group consisting of AP1 (c-Fos, c-Jun), cAMP response element-binding protein/CREB, GATA transcription factor, and NFkappaB, SP1, C/EBP, FOXO, SMAD transcription factor proteins, wherein the prognosis resp. the prediction and/or detection is further based on the activation status determined in step (vi).

In general, preferred embodiments of such methods become apparent in view of the above described steps and embodiments in connection with the method for stratification of a (cancer) patient.

By applying the methods of the present invention, especially methods according to the preferred embodiments described herein, it is possible to make a reliable prediction of the likelihood that (cancer) patients will develop a resistance to a certain therapeutic, or to determine if such a resistance already exists.

A further aspect of the present invention relates to a kit, comprising the following components:
- a first antibody directed against the epitope of a member of the ER family, said member being part of a transcription factor complex, and
- a second antibody directed against the epitope of a protein selected from the group consisting of TAFs, TBP, POLII, TFII, p300, CREP1, and CBP, wherein the protein is part of the same transcription factor complex as the above mentioned member of the ER family.

Preferably, such a kit is used in a method according to the present invention as described herein, preferably a method as described herein as preferred. The present invention therefore also relates to the specific use of such a kit in a method according to the present invention and, respectively, such a kit for use in a method according to the present invention.

In the context of the present invention, also the use of a first and a second antibody and, if applicable, of one or more further optional components (as respectively described above or herein below) in the preparation of a kit according to the present invention, preferably for use in a method according to the present invention, is disclosed.

Preferably, either through two secondary antibodies coupled to specific oligosequences, or through direct coupling of the oligo sequences to the primary antibodies, the PLA assay is developed and performed according to protocol.

Of course, depending on the intended use of such a kit, further/other antibodies directed against further/other epitopes of further/other proteins may be employed (in this regard, cf., in particular, the above described steps (ii) to (vi), wherein further targets for antibodies are referred to).

Preferably, (A) the first and the second antibody of the above described kit are each labeled with a DNA oligo, or (B) the kit additionally comprises a third and a fourth antibody being directed against the first and the second antibody, respectively, and the third and the fourth antibody being labeled with a DNA oligo.

A kit according to the invention may also comprise further components, such as circle forming oligonucleotides, enzymes such as a ligase and a polymerase allowing ligation and rolling circle amplification, respectively. Furthermore, wash buffers and brightfield- or fluorescent probes in the form of complimentary oligonucleotides might be added to such a kit. Also microscope slides, coverslips and mounting medium could be added to such a kit. Any buffer in such a kit could contain DAPI or any other nuclear stain in order to visualize the cell nucleus. In another embodiment of such a kit, a (primary) antibody might be added that contains both a fluorescent probe and an oligonucleotide probe. Such an antibody would fluoresce on its own and could at the same time be a partner in a PLA application.

With such a kit the methods of the invention can be performed in a secure and reproducible way.

In connection with the present invention, an automated equipment for performing the methods according to the invention may be used, i.e., (a) for carrying out the staining assays comprising any required incubation and washing steps, (b) for the acquisition of the images by illumination of the sample and storing the images in a digital file, or (c) for the processing and analysis of the digital images of the stained samples.

To use such automated equipment improves the reliability and repeatability of the results, enables digitization of the sample slide staining results such that the staining assay can be interpreted in an automated fashion by means of a computer algorithm. It also speeds up the handling of a larger number of samples.

For (targeted) therapy choice it is important to identify whether multiple signaling pathways in a tumor tissue sample of a cancer patient are active in the same cancer cell or in different cells, representing multiple cancer cell clones, or for example one pathway in a cancer cell and another pathway in a tumor associated fibroblast or immune cell (e.g. macrophage) or other cell type present in the tumor tissue. This can also be relevant for prognosis, e.g. an independent Wnt positive clone in the tissue may indicate a propensity for metastasis.

Current developments around synthetic lethality therapy: meaning a combination of drugs which target different signaling pathways (or other relevant targets) in cancer cells, these therapies are lethal to the cell only if both targets are present in the same cell, not if one target is present in one cancer cell clone and the other in another cancer cell clone or other cell type in the tissue.

The above described aspects and other aspects of the present invention will be more apparent from and elucidated with reference to the embodiments described hereinafter and, in particular, the patent claims as attached. Preferred embodiments of the present invention are defined in the dependent claims. It shall be understood that the methods of claims 1, 8 and 9, the kit of claim 10 and the uses of a kit of claims 11 to 13 have similar and/or identical preferred embodiments or, respectively, steps and features as defined in the dependent claims and as defined herein.

DETAILED DESCRIPTION OF EMBODIMENTS

As described above, the methods of the present invention allow for a reliable determination of the activity of certain pathways on protein levels. In particular, by using the proximity ligation assay it can be determined in which cells of a tissue sample the pathway is active. In this respect, it is also possible to provide evidence on the percentage of cancer cells in a tissue sample (as described above), preferably a tissue slide, which have the respective pathway activated. Furthermore, the methods described herein enable one to predict if certain (hormonal) therapies will be effective, whether resistance to (hormonal) treatment is expected or likely to develop, so that the matching therapy can be chosen depending on which pathway is found to be active.

It is preferred that the methods according to the invention (as described above) are performed on tissue samples in vitro, preferably on tissue slides.

The methods according to the invention can be advantageously combined with further, typically used stratification techniques. Such additional stratification tests can be made on the same tissue sample or on a different tissue sample obtained from the cancer patient. Furthermore, such addition stratification may be performed prior to the testing according to the invention, at the same time or later. For example, such additional testing can be performed by using IHC staining.

With respect to the antibodies that may be used in connection with the proximity ligation assay(s) used in a method of the invention (as described herein), it is to be noted that different antibodies may be utilized which carry different labels in different color channels, so as to a testing for more than one pathway can be made in parallel on the same sample. Furthermore, it may be suitable to label certain antibodies, e.g. anti ER antibodies, with labels in different color channels, so as to e.g. IHC and PLA staining can be made with the same antibodies.

As described above, particularly preferred methods according to one aspect of the present invention comprise the following step:

(i) determining the activation status of an ER and/or PR signaling pathway by applying a Proximity Ligation Assay to detect in a tissue sample of the (cancer) patient the presence of at least one member of the ER family, said at least one member being part of a transcription factor complex, and at least one protein selected from the group consisting of TAFs, TBP, POLII, TFII, p300, CREP1, and CBP, wherein the at least one protein is part of the same transcription factor complex.

Further preferred embodiments and features of methods according to the present invention are described above. Exemplary particularly preferred methods of the invention according to one aspect of the present invention comprise the following steps:

(i) determining the activation status of an ER and/or PR signaling pathway by applying a Proximity Ligation Assay to detect in a tissue sample of the (cancer) patient the presence of at least one member of the ER family, preferably an ER dimer, said at least one member being part of a transcription factor complex, and at least one protein selected from the group consisting of TAFs, TBP, POLII, TFII, p300, CREP1, and CBP, preferably p300, wherein the at least one protein is part of the same transcription factor complex, and (v) determining the activation status of the PI3K pathway by applying a Proximity Ligation Assay to detect in the same tissue sample of the (cancer) patient an active PKB/Akt protein by measuring the phosphorylation status of PBK/Akt, preferably wherein the patient is cancer patient, more preferably a breast cancer patient, preferably an ER and/or PR positive and HER2 negative breast cancer patient and, respectively, the tissue sample is a tumor tissue sample from a breast cancer patient, preferably from an ER and/or PR positive and HER2 negative breast cancer patient.

By employing such methods, basically four different test results are possible with four different treatment choices in an adjuvant setting (in all cases additional chemotherapy and radiation therapy are decided separately):

1. ER containing transcription factor complex (step (i)): positive pAkt (step (v)): negative
   → treatment choice: "endocrine treatment".
2. ER containing transcription factor complex (step (i)): positive pAkt (step (v)): positive
   → treatment choice: "endocrine treatment" and (potential new) inhibitors of the PI3K pathway.
3. ER containing transcription factor complex (step (i)): negative pAkt (step (v)): negative
   → no endocrine treatment, no PI3K pathway drugs (potentially with exception of PI3K pathway inhibitors downstream of pAkt, such as TORC1 and/or TORC2 inhibitors).
4. ER containing transcription factor complex (step (i)): negative pAkt (step (v)): positive
   → (potential new) inhibitors of the PI3K pathway.

It has to be noted that it is within the scope of the present invention to analyze the activity of two, three, more or all of the herein mentioned pathways (in this regard, cf. in particular steps (ii) to (vi) as described above), preferably by using the same tissue sample. This allows an improved choice of suitable treatment for the respective (cancer) patient.

For example, depending on the outcome of testings performed on the basis of the herein described methods suitable therapeutics for (hormonal) treatment and/or, for example, suitable PI3K pathway inhibitors can be chosen from currently approved drugs (by e.g. FDA, CFDA, EMA, etc.) or from drugs in clinical trials (cf. e.g. FIG. 2 for drugs addressing PI3K pathway) or future drugs not yet known to the public.

Figure 1:
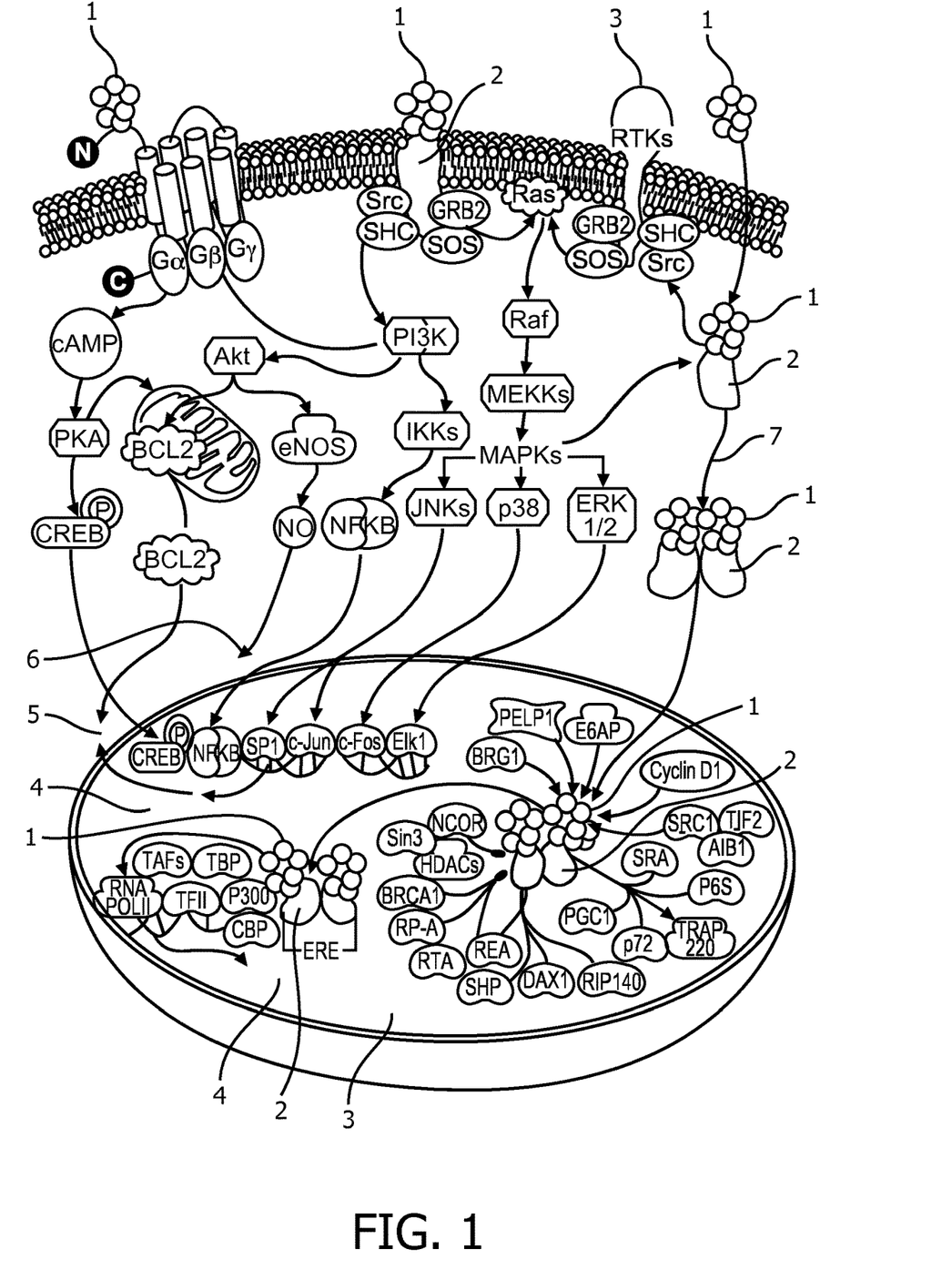
FIG. 1 schematically shows possible ER-pathways. In particular, the figure shows that ER itself may be part of a multi-component transcription factor complex, wherein all of the proteins of this complex are potential targets for the methods of the invention as described herein. It is also clear that via PI3K another transcription factor complex may be formed which involves NFkappaB.

As described above, FIG. 1 schematically shows possible ER-pathways. In particular, the figure shows that ER itself may be part of a multi-component transcription factor complex, wherein all of the proteins of this complex are potential targets for the methods of the invention as described herein. In FIG. 1 the reference numbers have the following meaning:

| | |
|---|---|
| 1 | Estrogen |
| 2 | Estrogen Receptor |
| 3 | Growth Factors |
| 4 | Gene Expression |
| 5 | Antiapoptosis |
| 6 | Vasodilation |
| 7 | Dimerization |
| 8 | Nucleus |

Figure 2:
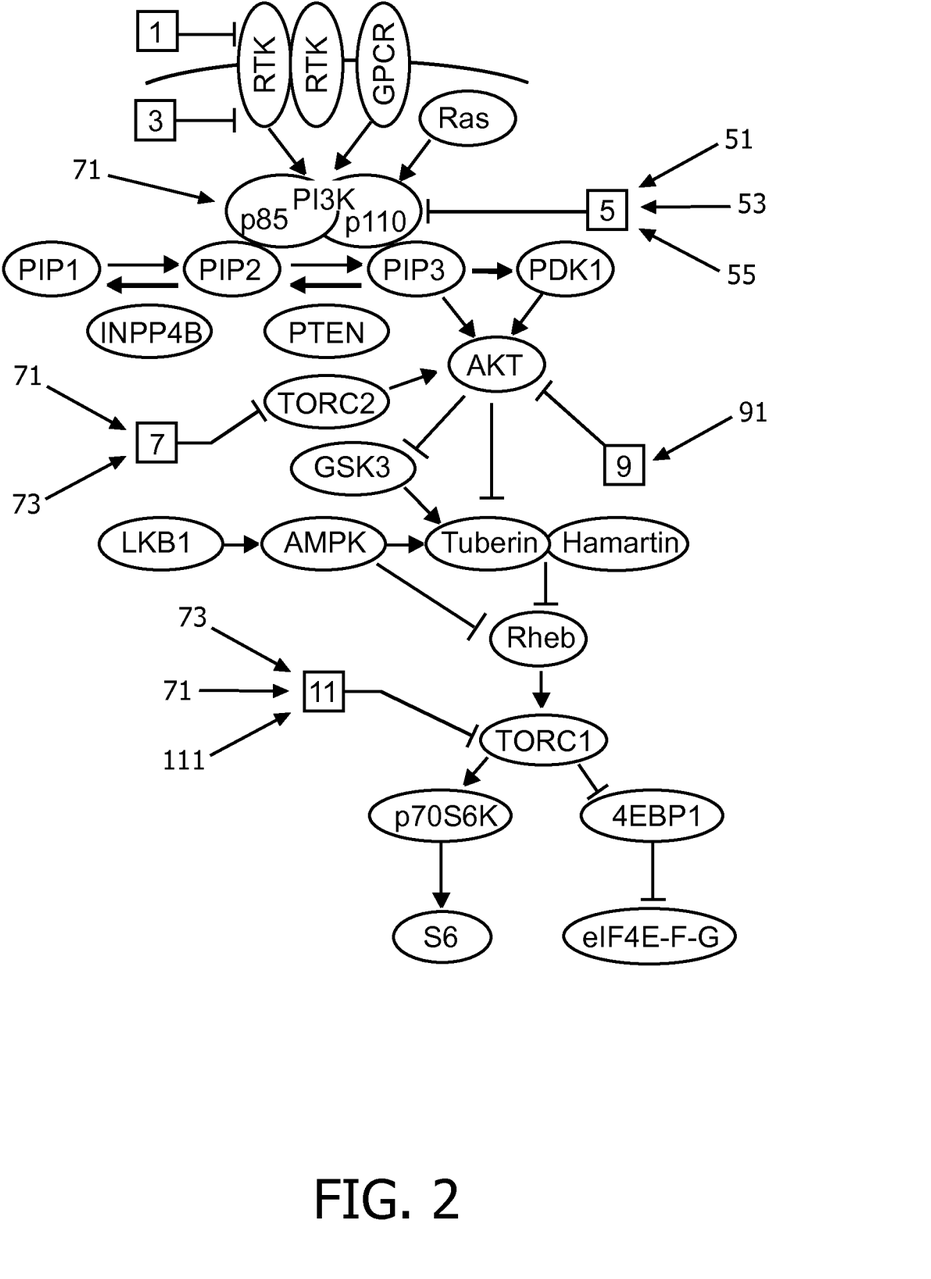
FIG. 2 exemplarily shows a flow chart illustrating the choice of a suitable therapy depending on the results of a preferred method according to the invention.

As described above, FIG. 2 exemplarily shows a flow chart illustrating the choice of a suitable therapy depending on the results of a preferred method according to the invention. In FIG. 2 the reference numbers have the following meaning:

| | |
|---|---|
| 1 | Antibodies |
| 3 | ATP-competitive inhibitors |
| 5 | ATP-competitive inhibitors |
| 7 | ATP-competitive inhibitors |
| 9 | ATP-competitive & allosteric inhibitors |
| 11 | ATP-competitive & FKBP12-mediated inhibitors |
| 51 | Possible position(s) of intervention/mode of action of the following drugs (Pan-Pi3K): BKM120 (Novartis) XL-147 (Exelixis) PX-866 (Oncothyreon) GDC-0941 (Genentech) CH51327909 (Chugai Pharma) |

| | -continued | |
|---|---|---|
| 53 | Possible position(s) of intervention/mode of action of the following drugs (P110δ-specific):<br>CAL-101 (Calistoga) | |
| 55 | Possible position(s) of intervention/mode of action of the following drugs (P110α-specific):<br>BYL719 (Novartis)<br>GDC-0032 (Genentech)<br>INK-1117 (Intellikine) | |
| 71 | Possible position(s) of intervention/mode of action of the following drugs (PI3K/mTOR):<br>PKI-587 (Pfizer)<br>BEZ235 (Novartis)<br>BGT226 (Novartis)<br>PF-4691502 (Pfizer)<br>GDC-0980 (Pfizer)<br>XL-765 (Exelixis)<br>SF1126 (Sernafor)<br>GSK1059615 (GSK) | |
| 73 | Possible position(s) of intervention/mode of action of the following drugs (TORC1/2):<br>INK-128 (Intellikine)<br>OSI-027 (Wyeth/Pfitzer)<br>AZD-8055 (Astrazeneca) | |
| 91 | Possible position(s) of intervention/mode of action of the following drugs (Akt):<br>AZD5363 (Astrazeneca)<br>GDC-0068 (Genentech)<br>GSK690693 (GSK)<br>VQD002 (Vloquest) | |
| 111 | Possible position(s) of intervention/mode of action of the following drugs (TORC1):<br>Everolimus/RAD001 (Novartis)<br>Temsirolimus/CCI-779 (Wyeth/Pfitzer)<br>Ridaforolimus/AP-23575 (Merck/Ariad) | |

As described above, the present invention may be performed by the use of an automated equipment for performing the methods according to the invention, i.e. (a) for stratification of a patient, preferably a cancer patient, for assessing the suitability of a therapy for the patient, (b) for the prognosis of the outcome of a disease, preferably cancer, of a patient, preferably a cancer patient, or (c) for the prediction and/or detection of therapy resistance of a patient, preferably a cancer patient, towards (hormonal) therapy, as respectively described above.

Preferably, the methods are thereby performed such that the readout is fluorescence.

In general, the tests described herein in connection with the methods of the present invention can be performed manually, but it is also possible to use automated equipment, such as e.g. the benchmark of Ventana (Roche), thereby increasing reproducibility.

EXAMPLES

Example 1

Indirect PLA assay to determine the activation status of an ER signaling pathway in cancer cell line samples spun on a substrate:

Two antibodies raised in different species (e.g. mouse and rabbit) are used, e.g. mouse antibody against an epitope on the Estrogen-ER dimer complex (Monoclonal Mouse Anti-Human Estrogen Receptor α, clone 1D5, Dako/Cat #M7047) and rabbit antibody against p300 (Anti-p300 mouse anti-human mAb, clone NM-11, Millipore/Cat #NA46-100UG or Anti-p300 CT mouse anti-human mAb, clone RW 128, Millipore/Cat #05-257).

| Protocol: | |
|---|---|
| Deparaffinization: 3 × 10 min xylene, 5 min 100% EtOH, short 100% EtOH and 70% EtOH, tap water | 40 min |
| Antigen retrieval (optimum treatment to be established for every new antibody): 20-45 min 95° C., pH 6 or pH 9, cooling to RT, 10-20 min Wash 1-2× in PBS | 45 min |
| Blocking with Blocking Solution from the PLA kit: 1 drop per 1 cm2, incubation 30 min, 37° C., humidified Drip of Blocking Solution (do not wash) | 30 min |
| Incubation with 2 unlabelled primary antibodies from different species (e.g. mouse and rabbit), diluted in 0.1% BSA/PBS for 60 min, RT | 60 min |
| Wash 2 × 5 min in WashBuffer A | 10 min |
| Incubation with 2 PLA probes: e.g. PLUS-labeled-anti-mouse-antibody and MINUS-labeled-anti-rabbit-antibody in 1:5 in Antibody Diluent (AD) for 1 hr, 37° C., in the dark, humidified | 60 min |
| Wash 2 × 5 min in WashBuffer A (= 10 mM Tris/150 mM NaCl/0.05% Tween ™ 20) | 10 min |
| Incubation with Ligation mixture 1:5 in MQ and 1:40 ligase for 30 min, 37° C., in the dark, humidified | 30 min |
| Wash 2 × 2 min in WashBuffer A | 4 min |
| Incubation with Amplification Mixture 1:5 in MQ and 1:80 polymerase for 100 min, 37° C., in the dark, humidified (fluorescent probe included here as well) | 100 min |
| Wash 2 × 10 min in 1× WashBuffer B (= 200 mM Tris/100 mM NaCl) | 20 min |
| Wash 1 min in 0.01× WashBuffer B (= 2 mM Tris/1 mM NaCl) | 1 min |
| Let slide air-dry at RT in the dark | 10 min |
| Mounting with Duolink II Mounting Medium, wait at least 15 min before imaging | 15 min |

Image analysis. (Number of PLA dots per cell or per cell compartment is counted either manually or software-aided.)

Example 2

Direct PLA assay to detect phosphorylation status (=activation status) of Akt (to be made in addition to the assay of Example 1):

Two antibodies are used (can be form the same species: e.g. mouse antibody against Akt1 (F-8L, Santa Cruz Biotech) and another mouse antibody against phospho-Akt (18F3.H11, Abcam, ab105731))

| Protocol: | |
|---|---|
| Deparaffinization: 3 × 10 min xylene, 5 min 100% EtOH, short 100% EtOH and 70% EtOH, tap water | 40 |
| Antigen retrieval (to be tested for every new antibody): 20-45 min 95° C., pH 6 or pH 9, cooling to RT, 10-20 min Wash 1-2× in PBS | 45 |
| Blocking with Blocking Solution from the PLA kit: 1 drop per 1 cm2, incubation 30 min, 37° C., | 30 |

-continued

| Protocol: | |
|---|---|
| humidified | |
| Drip of Blocking Solution (do not wash) | |
| Incubation with 2 primary antibodies (could be from same or different species) conjugated to 2 PLA probes (PLUS and MINUS oligonucleotides) in buffer PBS/0.1% BSA/1:20 Assay Reagent for 1 hr, RT, in the dark, humidified | 60 |
| Wash 2 × 5 min in WashBuffer A (= 10 mM Tris/150 mM NaCl/0.05% Tween ™ 20) | 10 |
| Incubation with Ligation mixture 1:5 in MQ and 1:40 ligase for 30 min, 37° C., in the dark, humidified | 30 |
| Wash 2 × 2 min in WashBuffer A | 4 |
| Incubation with Amplification Mixture 1:5 in MQ and 1:80 polymerase for 100 min, 37° C., in the dark, humidified (fluorescent probe included here as well) | 100 |
| Wash 2 × 10 min in 1× WashBufferB (= 200 mM Tris/100 mM NaCl) | 20 |

Example 3

3.1 IHC Assays for ER and p300 in Both ER+ (MCF7) and ER− (SKBR3) Cell Lines IHC assays for ER and p300 were first performed in both ER+ (MCF7) and ER− (SKBR3) cell lines.

Figure 3:
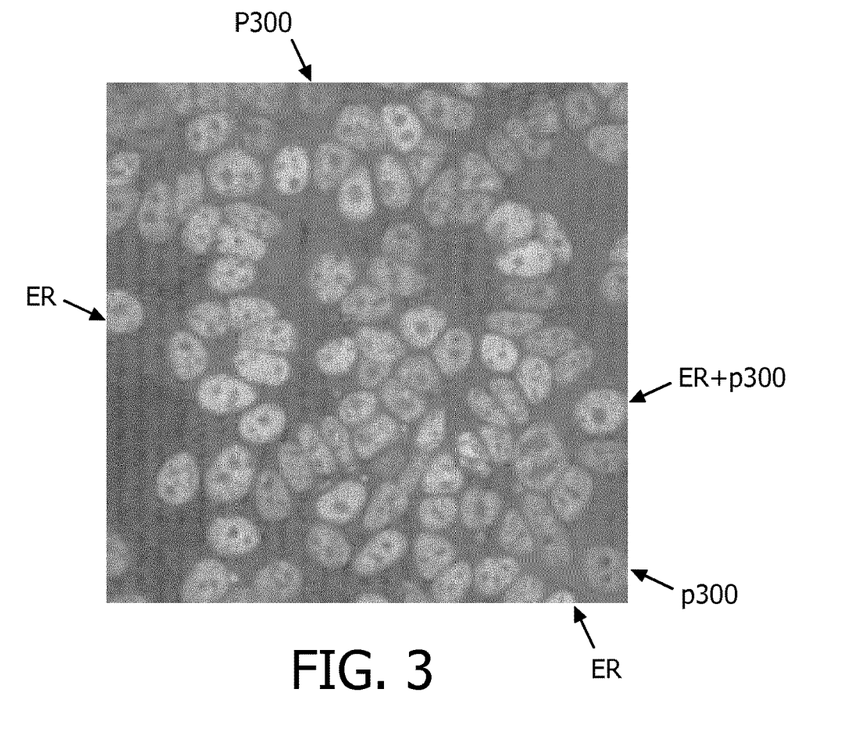
FIGS. 3 to 6 show results of IHC and PLA assays against ER and p300 (in this regard, cf. below, example 3).

The analyses clearly showed that both ER and p300 are present in the nucleus of MCF7 cells in varying concentrations. In particular, in the original color images obtained from the stained IHC assay, a number of the cells were colored greenish, which indicates the presence of ER, a number of the cells were colored reddish, which indicates the presence of p300, and a number of the cells were colored yellowish, which indicates a combined signal (cf. FIG. 3, which shows a grayscale image that is based on an original color image obtained from the stained IHC assay; the reference numerals "ER", "p300", and "ER+p300" exemplarily point to cells indicates as ER, p300 or combined). The differences in color in the original color images (in FIG. 3 reduced to differences in brightness) indicate that the expressions and/or presence of both ER and p300 vary widely among the cells.

Figure 4:
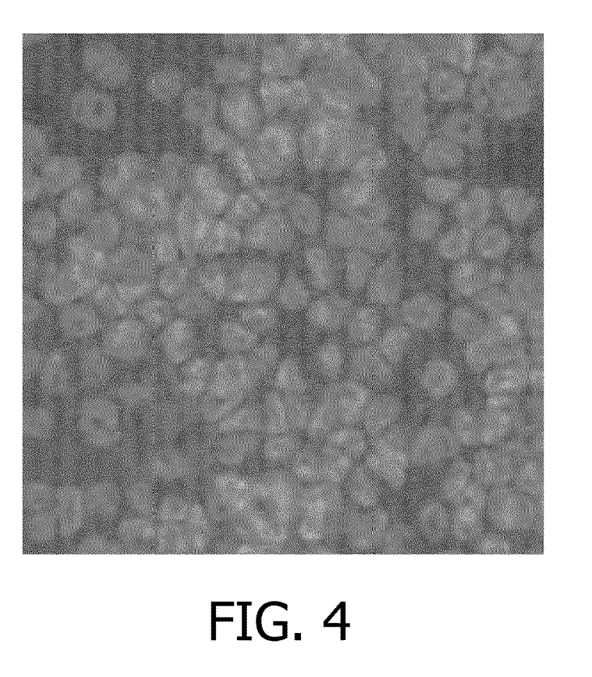

In SKBR3 cells, in contrast, only p300 can be found. In fact, SKBR3 cells do not show any signal in the ER channel leaving the nuclei reddish colored by the anti-p300 antibody (cf. FIG. 4, which shows a grayscale image that is based on an original color image obtained from the stained IHC assay; the cells visible in the image are colored reddish in the original color images, indicating the presence of only p300).

3.2 PLAs Against ER and p300 in Both ER+ (MCF7) and ER− (SKBR3) Cell Lines

PLAs against ER combined with p300 were performed in both ER+ (MCF7) and ER− (SKBR3) cell lines.

Figure 5:
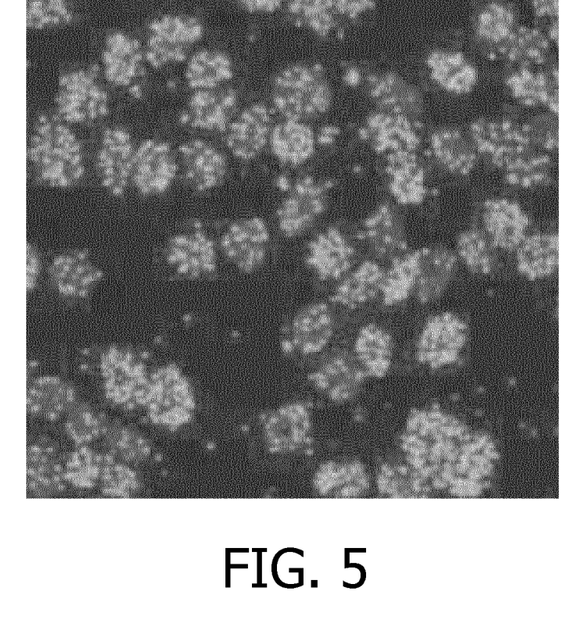
Figure 6:
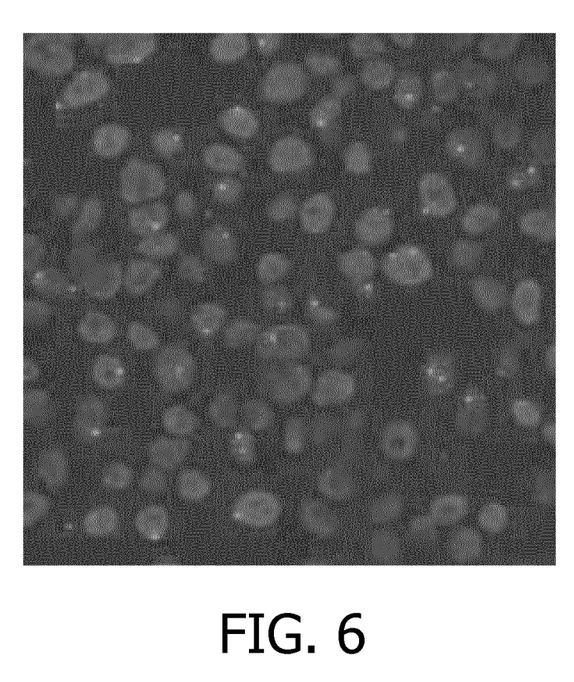

The results clearly indicated the locations in the nuclei of cells where both factors are present in the same complex. In particular, in the original color images obtained from the stained PLAs, a high numbers of active transcription factor complexes are indicated for the MCF7 cells by the high number of reddish colored dots (cf. FIG. 5, which shows a grayscale image that is based on an original color image obtained from the stained PLA for the MCF7 cells; the bright spots are colored reddish in the original images, indicating active transcription factor complexes). As expected from the IHC assay, there is some variation among cells. As also expected, SKBR3 cells show hardly any active transcription factor complexes (cf. FIG. 6, which shows a grayscale image that is based on an original color image obtained from the stained PLA for the SKBR3 cells).

Similar data are produced when performing a PLA against ER and the co-factor CREB (data not shown).

While the invention has been illustrated and additionally described in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that test methods are recited in mutually different dependent claims does not indicate that a combination of these methods cannot be used to advantage.

The invention claimed is:

1. A method for stratification of a patient for assessing suitability of a therapy for the patient suffering from an ER (estrogen receptor) and/or PR (progesterone receptor) positive and HER2 (human epidermal growth factor receptor 2) negative cancer, the therapy being directed towards a signaling pathway, comprising:
   (i) determining an activation status of an ER and/or PR signaling pathway by applying a Proximity Ligation Assay to detect in a tissue sample of the patient a presence of at least one member of the ER family, said at least one member being part of a transcription factor complex, and at least one protein selected from a group consisting of TAFs (TATA-binding protein associated factor), TBP (TATA-box binding protein), POLII (RNA polymerase II), TFII (transcription factor II), p300, CREB (cyclic-AMP response element-binding protein), and CBP (CREB binding protein), wherein the at least one protein is part of the same transcription factor complex,
   wherein the stratification is based on the activation status determined in (i) and the suitability of the therapy is assessed based on the stratification,
   wherein a signaling pathway of (i) is determined to be active, if the at least one ER family member is located in the nucleus in the Proximity Ligation Assay close proximity to the at least one protein selected from the group consisting of either TAFs, TBP, POLII, TFII, p300, CREB, and CBP.

2. The method of claim 1, wherein the at least one member of the ER family is an ER dimer.

3. The method of claim 1, additionally comprising:
   (ii) determining the activation status of a signaling pathway, which is different from the signaling pathway assessed in (i), by applying an in-situ staining assay to detect in the same or in a different tissue sample of the patient the presence of at least one member of the ER family and at least one protein selected from the group consisting of, c-Fos, c-Jun (AP1), SP1, CREB, GATA-transcription factor, NFkappaB family, c/EBP (CCAAT/enhancer binding protein) proteins, FOXO (Forkhead Box 0), SMAD transcription factor proteins,
wherein the stratification is further based on the activation status determined in (ii).

4. The method of claim 1, additionally comprising:
(iii) determining the phosphorylation status of at least one member of the ER family at serine 305 in the tissue sample of the patient,
wherein the stratification is further based on the phosphorylation status determined in (iii).

5. The method of claim 1, additionally comprising:
(iv) determining the activation status of one or more signaling pathways, which is/are different from the signaling pathway assessed in (i) and is/are selected from the group consisting of P13K (Phosphoinositide 3-kinase) pathway, Wnt pathway, hedgehog (HH) pathway, NFkappaB, Notch pathway, TGFbeta, FGF, VEGF, EMT, pathways, other nuclear receptor pathways, like the AR, RAR, PPAR, glucocorticoid, VitD pathways and growth factor pathways, like insulin GF and EGF, by applying an in-situ staining assay, wherein the same or a different tissue sample of the patient is used,
wherein the stratification is further based on the activation status determined in (iv).

6. The method of claim 1, additionally comprising:
(v) determining the activation status of the P13K pathway by applying an in-situ-staining assay to detect in the same or in a different tissue sample of the patient an active PKB (protein kinase B)/Akt (protein kinase B) protein by measuring the phosphorylation status of PBK/Akt,
wherein the stratification is further based on the activation status determined in (v).

7. The method of claim 1, additionally comprising:
(vi) applying an in-situ staining assay to detect in the same or in a different tissue sample of the patient the presence of at least one member of the ER family and at least one component which is expected to be present at any ERE (Estrogen Response Element) half-site or any non ERE site and/or wherein the at least one component is selected from the group consisting of AP1, cAMP response element-binding protein/CREB, GATA transcription factor, NFkappaB, SP1, C/EBP, FOXO, and SMAD transcription factor proteins,
wherein the stratification is further based on the detection in (vi).

* * * * *